(12) United States Patent
Nishtala

(10) Patent No.: US 8,986,230 B2
(45) Date of Patent: Mar. 24, 2015

(54) NG TUBE WITH GASTRIC VOLUME DETECTION

(75) Inventor: Vasu Nishtala, Plano, TX (US)

(73) Assignee: C. R. Bard, Inc., Murray Hill, NJ (US)

( * ) Notice: Subject to any disclaimer, the term of this patent is extended or adjusted under 35 U.S.C. 154(b) by 1358 days.

(21) Appl. No.: 12/669,783

(22) PCT Filed: Jul. 18, 2008

(86) PCT No.: PCT/US2008/070457
§ 371 (c)(1),
(2), (4) Date: Jun. 14, 2010

(87) PCT Pub. No.: WO2009/012441
PCT Pub. Date: Jan. 22, 2009

(65) Prior Publication Data
US 2010/0274225 A1 Oct. 28, 2010

Related U.S. Application Data

(60) Provisional application No. 60/950,686, filed on Jul. 19, 2007.

(51) Int. Cl.
*A61B 5/103* (2006.01)
*A61B 5/117* (2006.01)
(Continued)

(52) U.S. Cl.
CPC ............... *A61B 5/036* (2013.01); *A61B 5/4233* (2013.01); *A61B 5/42* (2013.01); *A61B 5/204* (2013.01); *A61B 5/4211* (2013.01); *A61B 5/4238* (2013.01)
USPC .......................................... 600/593; 600/561

(58) Field of Classification Search
CPC ........ A61B 5/036; A61B 5/037; A61B 5/053; A61B 5/42; A61B 5/4233; A61B 5/4211; A61B 5/204; A61B 5/205; A61J 15/0003; A61J 15/0015; A61J 15/0026; A61J 2015/008; A61J 2015/0084
USPC ................................ 600/561, 593; 607/40, 41
See application file for complete search history.

(56) References Cited

U.S. PATENT DOCUMENTS 5,279,157 A    1/1994   Mattis et al.
5,665,064 A *   9/1997   Bodicky et al. ............... 604/516

(Continued)

FOREIGN PATENT DOCUMENTS

WO      2007002084 A2    1/2007

OTHER PUBLICATIONS

Dec. 17, 2008 International Search Report in International Application No. PCT/US2008/070457 filed on Jul. 18, 2008.

(Continued)

*Primary Examiner* — Devin Henson
(74) *Attorney, Agent, or Firm* — Rutan & Tucker, LLP

(57) ABSTRACT

An enteral tube includes a built-in Gastric Residual Volume (GRV) detection sensor at the distal end and a GRV indicating device at the proximal end for indicating the current GRV without requiring the aspiration of any stomach contents. The enteral tube with integrated GRV detection sensor is flexible and long enough to be looped around within the stomach. Weights may be employed to keep the sensor located generally at the lowest portion of the gastric cavity. The GRV detection sensor may include a sealed air column terminating with a flexible membrane. When the enteral tube and sealed air column are inserted into the stomach and submerged in gastric contents, pressure is exerted against the flexible membrane, and therefore against the sealed air column. A pressure sensor detects the pressure within the sealed air column and provides a signal or level representative of the amount of gastric contents in the stomach.

9 Claims, 4 Drawing Sheets

(51) Int. Cl.
*A61B 5/00* (2006.01)
*A61B 5/03* (2006.01)
*A61B 5/20* (2006.01)

(56) References Cited

U.S. PATENT DOCUMENTS

| | | | | |
|---|---|---|---|---|
| 5,814,012 | A * | 9/1998 | Fleenor et al. | 604/26 |
| 6,351,993 | B1 * | 3/2002 | Schellenberg | 73/299 |
| 6,503,208 | B1 * | 1/2003 | Skovlund | 600/561 |
| 6,929,150 | B2 | 8/2005 | Muderlak et al. | |
| 7,572,235 | B2 * | 8/2009 | Holte | 600/561 |
| 7,818,155 | B2 * | 10/2010 | Stuebe et al. | 703/11 |
| 2005/0171468 | A1 | 8/2005 | Wood | |
| 2005/0215948 | A1 | 9/2005 | Adams | |
| 2006/0189894 | A1 * | 8/2006 | Tucci | 600/584 |
| 2007/0207554 | A1 * | 9/2007 | Lin et al. | 436/514 |
| 2008/0086076 | A1 * | 4/2008 | Gerber | 604/43 |
| 2009/0187164 | A1 * | 7/2009 | Rowe | 604/529 |
| 2010/0179417 | A1 * | 7/2010 | Russo | 600/424 |

OTHER PUBLICATIONS

Dec. 9, 2008 Written Opinion of the ISA in International Application No. PCT/US2008/070457 filed on Jul. 18, 2008.

Jan. 19, 2010 International Preliminary Report on Patentability in International Application No. PCT/US2008/070457 filed on Jul. 18, 2008.

* cited by examiner

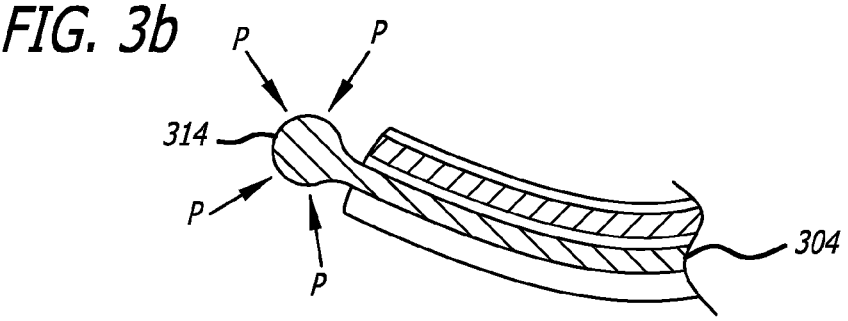
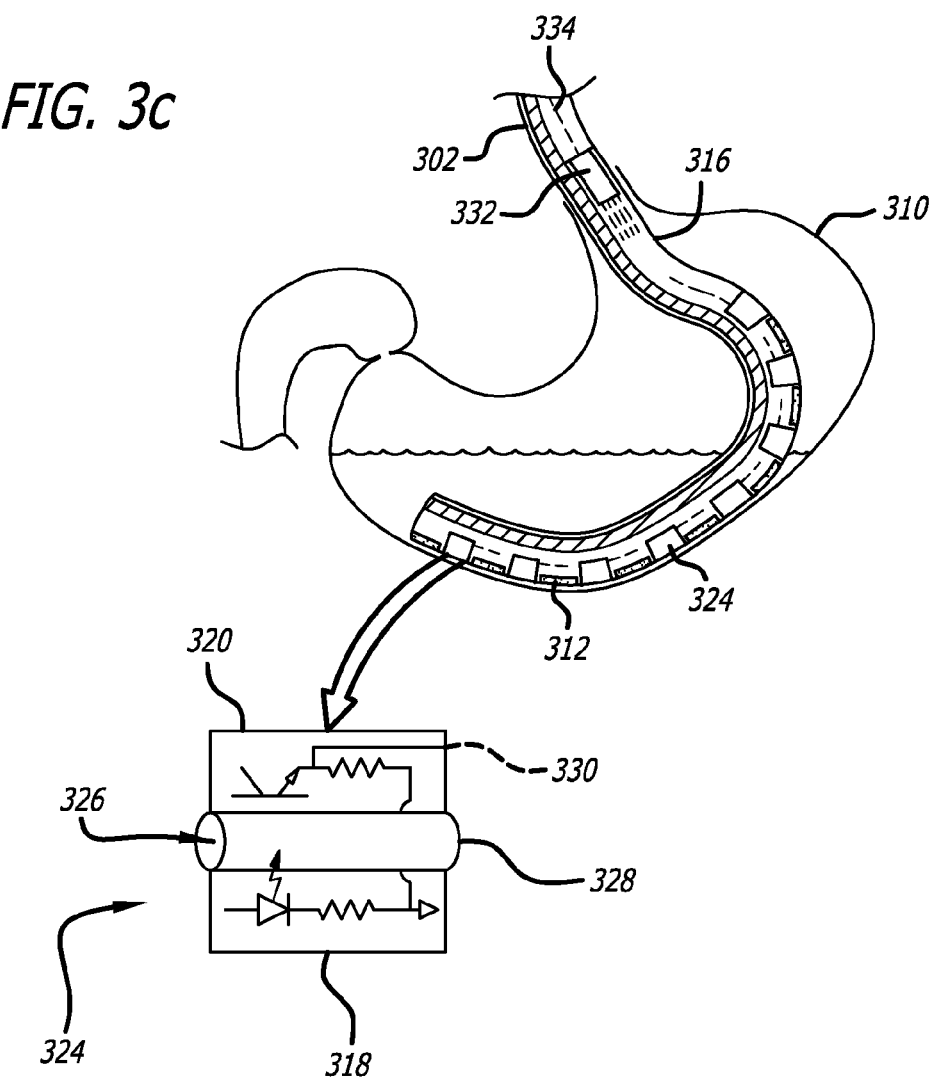

NG TUBE WITH GASTRIC VOLUME DETECTION

PRIORITY

This application is a U.S. national stage application under 35 USC§371 of International Application No. PCT/US2008/070457, field Jul. 18, 2008, which claims the benefit of priority to U.S. Provisional Patent Application No. 60/950,686, filed Jul. 19, 2007, each of which is incorporated by reference into this application as if fully set forth herein.

BACKGROUND

There are generally two ways to support patient nutrition for patients who are unable to self-feed orally in the usual manner—parenteral nutrition (by injection, e.g. IntraVenous (IV) feeding of electrolytes), and enteral nutrition (delivery directly into the GastroIntestinal (GI) tract). One disadvantage of IV feeding is that the patient's bowels may eventually shut down for lack of use, especially for patients with extended ICU stays. Enteral nutrition generally provides various physiologic and metabolic benefits as compared to parenteral nutrition. Thus, enteral tube feeding (e.g. Naso-Gastric (NG) tube feeding) is generally preferred when the patient's GI tract is functional and the patient is unable or unwilling to receive nutrition orally. In enteral tube feeding, a tube such as a NasoGastric (NG) tube is inserted through the patient's nasal passages and into the stomach. Nutrients (usually in the form of formula) is delivered directly to the patient's stomach through the NG tube.

However, enteral tube feeding can cause complications. Some patients receiving enteral tube feeding experience nausea and vomiting (which can lead to aspiration of stomach contents into the lungs and subsequent pneumonia) due to delayed gastric emptying. Even without vomiting, NG tube feeding can cause the contents of the stomach to reflux back into the lungs. When an NG tube is inserted into the stomach, the lower esophageal sphincter at the junction between the esophagus and the stomach may not be able to form an adequate seal, which can again lead to aspiration of stomach contents into the lungs and subsequent pneumonia. Other possible complications include diarrhea, constipation, and malabsorption/maldigestion (impaired absorption of nutrients).

Gastric Residual Volume (GRV) is the volume of residual gastric contents that remain in the stomach after a certain period of time has elapsed from an enteral feeding, and generally is an indication of how well the nutrients (e.g formula) are being absorbed by the stomach. High GRV levels can alert health care providers that there may be complications impairing gastric emptying and impending intolerance, and that subsequent feedings should be reduced or stopped altogether before vomiting or aspiration occurs. However, there is currently no direct and relatively immediate confirmation of emptying of the stomach after formula has been forced into the patient's stomach via an NG tube. Furthermore, even if the stomach empties, it cannot be immediately determined whether the formula is being tolerated (the nutrients are being absorbed), or whether the formula is just passing through the patient's digestive system, resulting in diarrhea, for example. To monitor tolerance and gastric emptying, a process referred to as GRV detection is currently employed.

In current GRV detection methodologies, a syringe or similar device is connected to the NG tube to extract the patient's stomach contents after a certain period of time. The amount of gastric contents extracted at that time is an indication of gastric emptying. The degree of gastric emptying along with other symptoms can provide an indication of gastric tolerance. Elevated GRV levels can be an indication of enteral tube feeding intolerance.

However, because the stomach contents extracted using this GRV detection procedure have an unpleasant odor and can produce biohazards, contamination, bacteria, and infections, there may be a reluctance on the part of the clinician to regularly perform the procedure. In addition, because GRV detection results in the removal of the stomach contents, the patient experiences a loss of nutrition if the gastric contents are not returned to the patient's stomach through the NG tube.

Thus, there is a need to perform GRV detection in a manner that is simpler, less unpleasant, does not produce biohazards, contamination, bacteria, and infections, and does not lead to a loss of nutrition by the patient. Such systems, apparatus and methods may lead to more regular testing of GRV detection, more frequent detection of enteral tube feeding intolerance, and faster implementation of corrective measures.

BRIEF SUMMARY

Accordingly, an enteral tube with GRV detection is described herein, the enteral tube in one embodiment including a built-in GRV detection sensor at the distal end (the end normally placed in the stomach). A volume indicating device such as a display device may be connected to or located at the proximal end (the end that remains outside the body), and indicates the current GRV without requiring the aspiration of any stomach contents. Thus, at any time the medical staff can utilize the volume indicating device to determine how nutrients provided to the patient through the enteral tube are being absorbed by the stomach.

The volume indicating device may be integrated into the enteral tube, or it may be separate from, but connectable to, the enteral tube. The enteral tube may include a funnel-shaped device fixedly attached or connectable to its proximal end for enabling nutrients such as formula to be delivered to the patient's stomach through the enteral tube. The sensor may be connected to the volume indicating device via a wire or other conductive element within the enteral tube, or through a wireless connection.

The enteral tube with a GRV detection sensor is flexible and may be long enough to be looped around within the stomach to access and conform to various regions within the gastric cavity and access the areas of the stomach at which the gastric contents may pool, regardless of the position of the patient. Weights may be employed within the GRV detection sensor and spaced at intervals to keep the sensor located generally at the lowest portion of the gastric cavity as determined by the position of the patient at all times. The enteral tube may also have a specific geometry (e.g. a flexible yet slightly curved pre-formed shape) that will allow the GRV detection sensor to be directed towards and access particular areas of the stomach when rotated at appropriate times during the insertion process.

The GRV detection sensor may include a sealed air column terminating with a flexible membrane. When the enteral tube and sealed air column are inserted into the stomach, it generally will come to rest in the lowest portion of the stomach due to the weights in the GRV detection sensor. To the extent that the sealed air column is submerged in gastric contents, pressure is exerted against the flexible membrane, and therefore against the sealed air column. The greater the height of the gastric contents, the greater the pressure. A pressure sensor detects the pressure within the sealed air column and provides a signal or level representative of the amount of gastric contents in the stomach to the volume indication device. The sealed air column may also be terminated with a sealed and flexible bulbous diaphragm, which can provide a larger signal or pressure reading to the pressure sensor representative of the amount of gastric contents in the stomach due to the larger surface area upon which pressure may be applied by the gastric contents.

The GRV detection sensor may alternatively be comprised of a plurality of fluid detection circuits, each fluid detection circuit including a photodiode and phototransistor pair surrounding a tube or chamber that is open at either end. The photodiode emits light that is detected by the phototransistor, and depending on how much light is detected by the phototransistor, a different amount of current flows through the phototransistor. The amount of light detected by the phototransistor 3 is dependent on whether air or fluid is present in the chamber. The plurality of fluid detection circuits are spaced along the distal portion of the enteral tube. When the enteral tube is inserted into the stomach, weights keep the sensor and therefore the fluid detection circuits near the bottom of the stomach. For every fluid detection circuit that is immersed in gastric contents, the gastric contents will flow into the chamber between the photodiode and phototransistor pair. Each photodiode and phototransistor pair detects whether there are gastric contents in the column at that point in the column, and provides a signal indicative of whether it detected the presence of gastric contents. In general, the higher the number of fluid detection circuits that detect gastric contents, the higher the level of gastric contents in the stomach.

The GRV detection device may alternatively be comprised of a separate GRV detection tube integrated with the enteral tube, an active suction device and a reservoir external to the enteral tube for temporarily storing gastric contents. When activated, the active suction device withdraws gastric contents from the stomach through the GRV detection tube and into the reservoir. After substantially all of the gastric contents have been withdrawn into the reservoir, a indication of the GRV can be obtained. After a GRV value has been obtained, the active suction device reverses direction and withdraws the collected gastric contents from the reservoir and pumps it back to the stomach via the GRV detection tube. The GRV detection device, including the GRV detection tube, the active suction device, and the reservoir may constitute a "closed" system, in that the gastric contents are not exposed to air or openings as it passes from the GRV detection tube to the active suction device and reservoir, and vice versa.

These and other embodiments, methods, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 3b is an illustration of an exemplary GRV detection sensor including a sealed air column terminating with a flexible and bulbous diaphragm.

FIG. 3c is an illustration of an exemplary GRV detection sensor including a plurality of fluid detection circuits, each fluid detection circuit including a photodiode and phototransistor pair surrounding a tube or chamber that is open at either end.

DETAILED DESCRIPTION

The following detailed description should be read with reference to the drawings. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Embodiments described herein relate generally to GRV detection, and specifically to an enteral tube with GRV detection. In one embodiment, an enteral tube such as an NG tube includes a built-in GRV detection sensor at the distal end (the end normally placed in the stomach). An indicating device such as a display device may be connected to or located at the proximal end (the end that remains outside the body), and indicates the current GRV without requiring the aspiration of any stomach contents. Thus, at any time the medical staff can utilize the display device to determine how the formula is being absorbed by the stomach.

Figure 1:
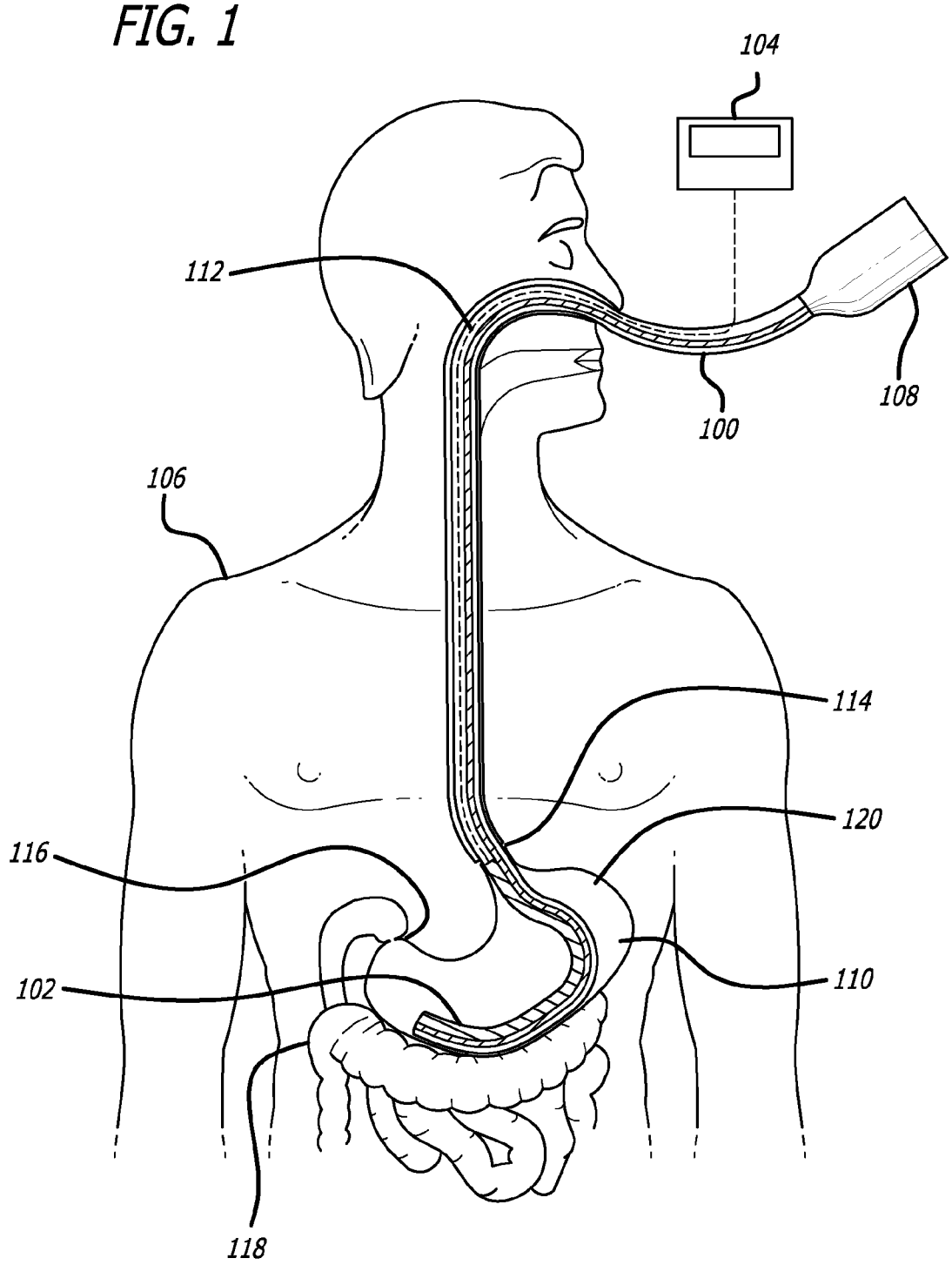
FIG. 1 illustrates an exemplary enteral tube with an integrated GRV detection sensor inserted into a patient.

FIG. 1 illustrates an exemplary enteral tube (which is shown in FIG. 1 as a NasoGastric (NG) tube 100) with an integrated GRV detection sensor 102 inserted into a patient 106. A volume indicating device 104 may also be integrated into the NG tube 100, or it may be separate from, but connectable to, the enteral tube as shown in FIG. 1. The volume indicating device may be a digital or analog display, a paper printout, or other indicating means and associated circuitry well-known to those skilled in the art. The NG tube 100 may include a funnel-shaped device 108 fixedly attached or connectable to its proximal end for enabling nutrients such as formula to be delivered to the patient's stomach 110 through the NG tube 100. The sensor 102 may be connected to the volume indicating device 104 via a wire or other conductive element 112 within the enteral tube 100 as shown in FIG. 1, or through a wireless connection.

The gastric cavity or stomach 110 has structures for providing a seal, including a lower esophageal sphincter 114 at the transition to the esophagus and a pyloric sphincter 116 between the stomach and the duodenum 118. These structures help keep gastric contents within the stomach, regardless of the position of the patient. The fundus 120 is the portion of the stomach at which most of the gastric contents will pool when the patient is in the supine position, and thus it is important that the GRV detection sensor 102 have the ability to be placed near or within the fundus. Because the GRV detection sensor 102 measures the volume of gastric contents present in the stomach, accurate placement of the sensor within the gastric contents can lead to a more accurate reading.

Figure 2:
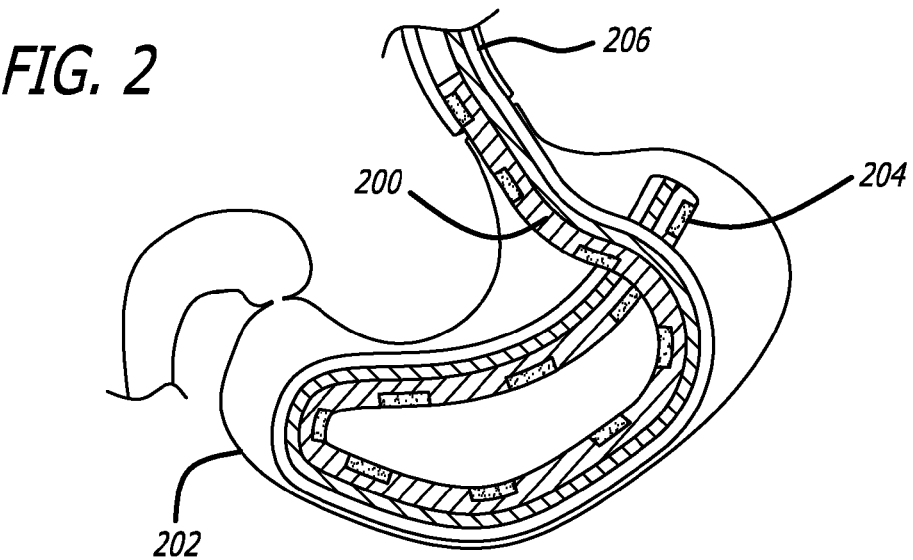
FIG. 2 is an illustration of an exemplary enteral tube with a GRV detection sensor which is flexible and long enough to be looped around within the stomach.

FIG. 2 is an illustration of an exemplary enteral tube 206 with a GRV detection sensor 200 according to one embodiment described herein which is flexible and long enough to be looped around within the stomach 202 to access and conform to various regions within the gastric cavity and access the areas of the stomach at which the gastric contents may pool, regardless of the position of the patient. One or more weights 204 may be employed within the GRV detection sensor 200 and spaced at intervals to keep the sensor located generally at the lowest portion of the gastric cavity 202 as determined by the position of the patient at all times. The enteral tube 206 may also have a specific geometry (e.g. a flexible yet slightly curved pre-formed shape) that will allow the GRV detection sensor 200 to be directed towards and access particular areas of the stomach 202 when rotated at appropriate times during the insertion process.

Figure 3A:
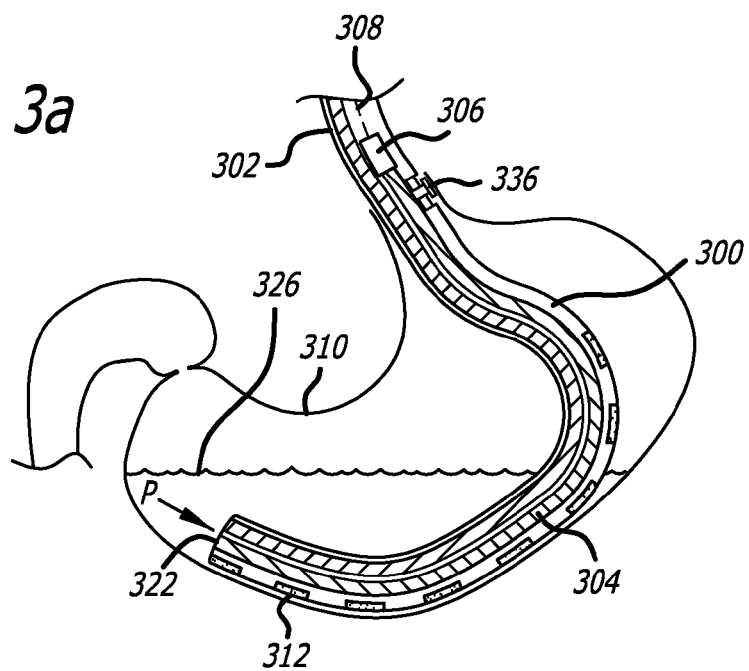
FIG. 3a is an illustration of an exemplary GRV detection sensor including a sealed air column terminating with a flexible membrane.

In one embodiment of the GRV detection sensor 300 described herein and shown in FIG. 3a, the sensor may be integrated within the distal end of the enteral tube 302, and includes a sealed air column or chamber 304 at ambient atmospheric pressure terminated with a flexible membrane 322. In one embodiment, the sealed air column may include a valve 336 that may be temporarily opened and closed to ensure that the sealed air column is at ambient atmospheric pressure (i.e. the air pressure of the surroundings of the patient). When the enteral tube 302 and therefore the sealed air column 304 are inserted into the stomach 310, it generally will come to rest in the lowest portion of the stomach 310 due to weights 312. To the extent that the sealed air column 304 is submerged in gastric contents 326, a pressure P is exerted against the flexible membrane 322, and therefore against the sealed air column 304. The greater the height H of the gastric contents, the greater the pressure P. A pressure sensor 306 detects the pressure P within the sealed air column 304 and, depending on the value of P, provides a signal or level representative of the amount of gastric contents in the stomach to the volume indication device (not shown in FIG. 3a), in one embodiment through conductive element 308. Pressure sensors 306 are known to those skilled in the art. One exemplary line of pressure sensors is the Honeywell line of silicon pressure sensors, and one exemplary pressure sensor is described in the datasheet for the Honeywell DC001NGC4, the contents of which are incorporated by reference herein.

FIG. 3b illustrates another embodiment described herein in which the sealed air column 304 terminates in a sealed and flexible bulbous diaphragm 314, which can provide a larger signal or pressure reading to the pressure sensor (not shown in FIG. 3b) representative of the amount of gastric contents in the stomach due to the larger surface area upon which pressure P may be applied by the gastric contents. The basic principles of the GRV detection sensor 300 in FIGS. 3a and 3b are described in U.S. Pat. No. 6,351,993, the contents of which are incorporated by reference herein.

FIG. 3c illustrates yet another embodiment described herein in which the GRV detection sensor 316 is comprised of a plurality of fluid detection circuits 324, each fluid detection circuit including a photodiode 318 and phototransistor 320 pair surrounding a tube or chamber 328 that is open at either end. The photodiode 318 emits light that is detected by the phototransistor 320, and depending on how much light is detected by the phototransistor, a different amount of current flows through the phototransistor. The amount of light detected by the phototransistor 320 is dependent on whether air or fluid is present in the chamber 328. Fluid detection circuits 324 are known to those skilled in the art. An example of a fluid detection circuit is disclosed in OPTEK Technology Inc.'s OPB350 series tube liquid sensor data sheet, the contents of which are incorporated by reference herein.

The plurality of fluid detection circuits 324 are spaced along the distal portion of the enteral tube 302. When the enteral tube 302 is inserted into the stomach 310, weights 312 keep the sensor 316 and therefore the fluid detection circuits 324 near the bottom of the stomach 310. For every fluid detection circuit 324 that is immersed in gastric contents, the gastric contents will flow into the chamber 328 between the photodiode 318 and phototransistor 320 pair. Each photodiode 318 and phototransistor 320 pair detects whether there are gastric contents in the column at that point in the column, and provides a signal 330 indicative of whether it detected the presence of gastric contents. The signals 330 may be sent directly to the volume indication device (not shown in FIG. 3c), or alternatively may be sent to an optional compilation circuit 332, which provides a single signal 334 to the volume indication device indicative of how many fluid detection circuits 324 actually detected gastric contents. In general, the higher the number of fluid detection circuits 324 that detect gastric contents, the higher the level of gastric contents in the stomach.

Figure 4:
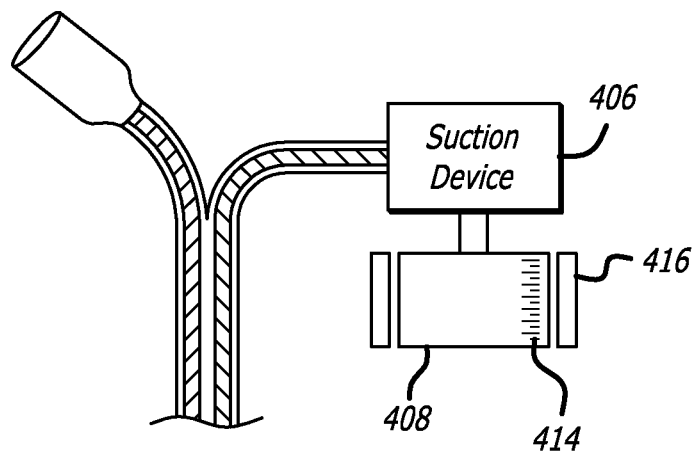
FIG. 4 is an illustration of an exemplary enteral tube including a GRV detection device having a separate GRV detection tube, an active suction device and a reservoir for temporarily storing gastric contents.
Figure 4:
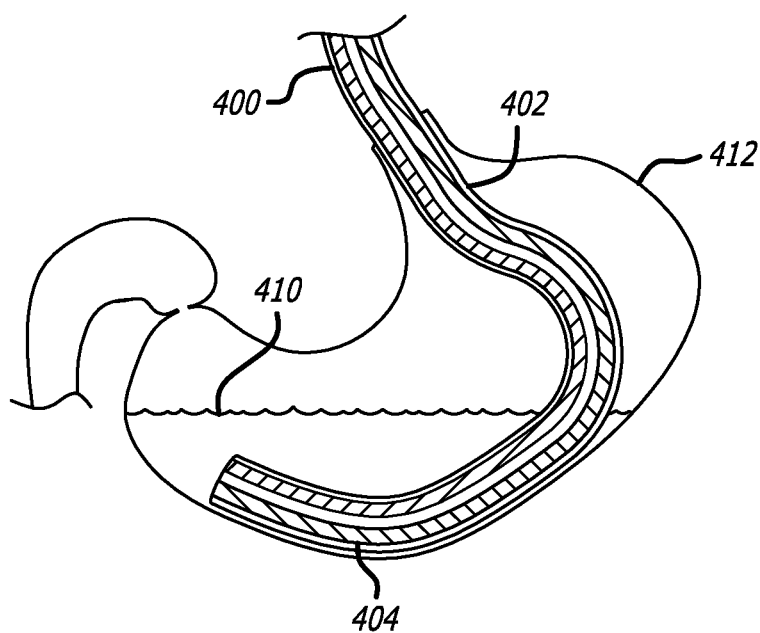

FIG. 4 is an illustration of an exemplary enteral tube 400 including a GRV detection sensor 402 according to another embodiment described herein. In FIG. 4, the GRV detection sensor 402 includes a separate GRV detection tube 404 and a suction device 406. The GRV detection tube 404 is coupled to the enteral tube 400, either by being integrally formed with the enteral tube or being removably or fixedly attached to the enteral tube. A reservoir 408 is coupled to the suction device 406 for temporarily storing gastric contents and acting as a volume indicating device. The suction device 406 may include a controllable pump. When activated, the suction device 406 withdraws gastric contents 410 from the stomach 412 through the GRV detection tube 404 and into reservoir 408. After substantially all of the gastric contents 410 have been withdrawn into the reservoir 408, a indication of the GRV can be obtained. In one embodiment, the gastric contents can be seen inside the reservoir 408, and markings 414 on the reservoir provide a visual indication of the GRV. In other embodiments, the reservoir 408 may employ an electronic "eye" 416 that senses the gastric contents level on a real-time basis, either by continuously providing a total GRV value or by providing a GRV value at periodic intervals. Either case is considered to be "continuous" monitoring as defined herein.

After a GRV value has been obtained, the suction device 406 may be activated to reverse direction and withdraw the collected gastric contents from the reservoir 408 and pump it back to the stomach via the GRV detection tube 404. In one embodiment described herein, the GRV detection sensor 402 including the GRV detection tube 404 and the suction device 406, along with the reservoir 408, form a "closed" system in that the gastric contents are not exposed to air or openings as it passes from the GRV detection tube to the active suction device and reservoir, and vice versa. In a closed system, the chance of leakage of aspirated fluid, biohazards, contamination, bacteria, and infections is greatly reduced.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A Gastric Residual Volume (GRV) detection system comprising:
   an enteral tube including a lumen to deliver nutrients to a patient;
   a GRV detection sensor directly coupled to the enteral tube to sense and provide an indication of GRV, the GRV detection sensor comprising a plurality of fluid detection circuits to provide an indication of whether gastric contents have been detected to the volume indicating device, each fluid detection circuit comprising:
      a light emitting photodiode;
      a phototransistor to detect light emitted from the photodiode; and
      a chamber coupled between the photodiode and the phototransistor and having open ends to allow gastric contents to flow into the chamber and alter an amount of light detected by the phototransistor; and
   a volume indicating device communicatively coupled to the GRV detection sensor to enable receipt of the indication of the GRV from the GRV detection sensor and to display the GRV.

2. The GRV detection system according to claim 1, the GRV detection sensor configured to sense and provide the indication of the GRV without a need to withdraw gastric contents from the patient's stomach.

3. The GRV detection system according to claim 1, the volume indicating device configured to indicate the GRV based on how many of the fluid detection circuits indicate that gastric contents have been detected.

4. The GRV detection system according to claim 1, further comprising a compilation circuit communicatively coupled between the plurality of the fluid detection circuits and the volume indicating device to provide a single indication of the GRV to the volume indicating device in accordance with a number of fluid detection circuits indicating that gastric contents have been detected.

5. The GRV detection system according to claim 1, wherein the CRY detection sensor comprises a GRV detection tube and a suction device coupled together and configured to withdraw gastric contents from the patient's stomach through the GRV detection tube using the suction device, and wherein the volume indicating device comprises a reservoir coupled to the suction device to store the withdrawn gastric contents.

6. The GRV detection system according to claim 1, the GRV detection sensor including one or more weights.

7. The GRV detection system according to claim 6, the weights spaced out at intervals to allow the GRV detection sensor to flex.

8. A method for detecting Gastric Residual Volume (GRV), comprising:
   inserting an enteral tube and a GRV detection sensor comprising a plurality of fluid detection circuits coupled to the enteral tube into a patient's stomach, wherein each of the fluid detection circuits individually provides an indication of whether gastric contents have been detected by that fluid detection circuit, each fluid detection circuit comprising:
      a light emitting photodiode;
      a phototransistor to detect light emitted from the photodiode; and
      a chamber coupled between the photodiode and the phototransistor and having open ends to allow gastric contents to flow into the chamber and alter an amount of light detected by the phototransistor;
   sensing and providing an indication of GRV; and
   receiving the indication of the GRV from the GRV detection sensor and displaying the GRV.

9. A Gastric Residual Volume (GRV) detection sensor, comprising a plurality of fluid detection circuits to provide an indication of whether gastric contents have been detected, each fluid detection circuit including:
   a light emitting photodiode;
   a phototransistor to detect light emitted from the photodiode; and
   a chamber coupled between the photodiode and the phototransistor and having open ends to allow gastric contents to flow into the chamber and alter an amount of light detected by the phototransistor, the GRV varying in accordance with a number of fluid detection circuits indicating that gastric contents have been detected.

* * * * *